(12) United States Patent
Paz

(10) Patent No.: US 8,471,231 B2
(45) Date of Patent: Jun. 25, 2013

(54) OPTICAL DROP DETECTOR SYSTEM FEATURING A PLURALITY OF LIGHT PULSES FOR DETECTING A PLURALITY OF FLOWS

(75) Inventor: Ilan Paz, Gush Etzion (IL)

(73) Assignee: Flowsense Ltd, Misgav (IL)

( * ) Notice: Subject to any disclaimer, the term of this patent is extended or adjusted under 35 U.S.C. 154(b) by 128 days.

(21) Appl. No.: 12/843,106

(22) Filed: Jul. 26, 2010

(65) Prior Publication Data
US 2011/0046899 A1    Feb. 24, 2011

Related U.S. Application Data

(63) Continuation of application No. 11/794,843, filed as application No. PCT/IL2006/000065 on Jan. 17, 2006, now Pat. No. 7,763,877.

(30) Foreign Application Priority Data

Jan. 20, 2005   (IL) .......................................... 166400

(51) Int. Cl.
*G01N 21/35* (2006.01)

(52) U.S. Cl.
USPC ....................................... 250/573; 73/861.41

(58) Field of Classification Search
USPC ................................ 250/573–577; 73/861.41
See application file for complete search history.

(56) References Cited

U.S. PATENT DOCUMENTS

| | | | |
|---|---|---|---|
| 3,641,543 A | 2/1972 | Rigby | |
| 3,712,132 A | 1/1973 | Thys et al. | |
| 3,859,854 A | 1/1975 | Dye et al. | |
| 3,870,065 A | 3/1975 | Minns, Jr. | |
| 3,871,229 A | 3/1975 | Fletcher | |
| 4,038,982 A * | 8/1977 | Burke et al. | .................... 604/65 |

(Continued)

FOREIGN PATENT DOCUMENTS

| | | |
|---|---|---|
| JP | H02151724 | 12/1998 |
| JP | H04032035 | 1/2006 |

(Continued)

OTHER PUBLICATIONS

Brazilian Application PI0008757-2 Office Action.

(Continued)

*Primary Examiner* — Tony Ko
(74) *Attorney, Agent, or Firm* — Graeser Associates International Inc; Dvorah Graeser

(57) ABSTRACT

The invention provides an optical drop detection system (10), for a low-flow metering device of the type having a drop generator 12, 24, (19), the system comprising at least one optical transmitter (26) which produces a plurality of light beam pulses (28) of microsecond duration and at millisecond intervals, and at least one optical receiver (33) positioned to register receipt of the light pulses (28) transmitted through the path of drops (18) generated by the drop generator (12, 24, 19) and to record the number of pulses which hit a given drop and which do not register on the receiver (32), the frequency and strength of the pulses being calibrated so that a single drop is impinged upon by a plurality of pulses, and further comprising automatic feed-back means for adjusting the parameters of interaction between the at least one optical transmitter (26) and the at least one optical receiver (32) to produce and maintain a predetermined minimum and a predetermined maximum number of hits per drop.

13 Claims, 4 Drawing Sheets

U.S. PATENT DOCUMENTS

| | | | |
|---|---|---|---|
| 4,051,431 A | 9/1977 | Wurster | |
| 4,099,412 A | 7/1978 | Nehrbass | |
| 4,261,388 A | 4/1981 | Shelton | |
| 4,321,461 A | 3/1982 | Walter, Jr. et al. | |
| 4,325,483 A * | 4/1982 | Lombardo et al. | 209/3.1 |
| 4,343,316 A | 8/1982 | Jespersen | |
| 4,448,207 A | 5/1984 | Parrish | |
| 4,484,582 A | 11/1984 | Rottenberg et al. | |
| 4,520,667 A | 6/1985 | Nelson | |
| 4,532,936 A | 8/1985 | LeVeen et al. | |
| 4,554,687 A | 11/1985 | Carter et al. | |
| 4,559,831 A | 12/1985 | Prestele | |
| 4,650,464 A | 3/1987 | Ruiz et al. | |
| 4,683,748 A | 8/1987 | Carter | |
| 4,718,896 A | 1/1988 | Arndt et al. | |
| 4,740,200 A | 4/1988 | Theeuwes | |
| 4,827,766 A | 5/1989 | Nelson | |
| 4,936,828 A * | 6/1990 | Chiang | 604/65 |
| 4,946,439 A | 8/1990 | Eggers | |
| 5,098,408 A | 3/1992 | Tarzian | |
| 5,186,057 A * | 2/1993 | Everhart | 73/861.41 |
| 5,267,978 A | 12/1993 | Dirr, Jr. et al. | |
| 5,571,964 A | 11/1996 | Sawada et al. | |
| 5,581,026 A | 12/1996 | Sawada et al. | |
| 5,698,793 A | 12/1997 | Carmichael | |
| 5,769,087 A | 6/1998 | Westphal et al. | |
| 6,372,506 B1 | 4/2002 | Norton | |
| 6,447,684 B2 | 9/2002 | Parekh et al. | |
| 6,640,649 B1 | 11/2003 | Paz | |
| 7,563,243 B2 | 7/2009 | Mendels | |
| 2003/0045840 A1 | 3/2003 | Burko | |
| 2010/0022967 A1 | 1/2010 | Mendels | |

FOREIGN PATENT DOCUMENTS

| | | |
|---|---|---|
| WO | WO0042394 | 7/2000 |
| WO | WO2004045704 | 6/2004 |
| WO | WO2010041458 | 12/2010 |
| WO | WO2010041563 | 12/2010 |

OTHER PUBLICATIONS

International Search Report for PCT/IL2006/000065.
Written Opinion for PCT/IL2006/000065.
Chinese application 201010002058.1 Office Action.
Japanese application 2007-551812 Office Action.
International search Report for PCT/IL2000/000027.

* cited by examiner

OPTICAL DROP DETECTOR SYSTEM FEATURING A PLURALITY OF LIGHT PULSES FOR DETECTING A PLURALITY OF FLOWS

This Application is a Continuation Application of, and claims priority from, U.S. patent application No. Ser. 11/794,843, filed on Apr. 1 2008, which is a national phase of, and claims priority from, PCT Application No. PCT/IL2006/000065, filed on Jan. 17 2006, which claims priority from Israeli Application No. IL 166400, filed on Jan. 20 2005, all of which are hereby incorporated by reference as if fully set forth herein.

The present invention relates to low-flow metering of fluids.

More particularly, the invention provides an optical system for measuring low flow-rates of a fluid that passes a measuring point in the form of discrete drops.

As is known, conventional flow meters are of no use for the registration of very slow flow rates. However as the metering of slow flows is needed in research and in medical applications, many specialized devices for this purpose have been developed. Typical medical applications include fluid and food infusions and measurement of blood flow entering/leaving the patient. In some situations measurement of urine output may be needed, and such devices would definitely be useful for measuring IV flow.

A review of the prior art has been provided in the present inventor's earlier U.S. Pat. No. 6,640,649 B1 that is hereby incorporated for reference. Further examples of prior art are seen in U.S. Pat. Nos. 3,870,065 to Minns, Jr., 4,650,464 to Ruiz et al., 4,718,896 to Arndt et al and 4,946,439 to Eggers.

In said previous patent there is described a device wherein droplets are generated and electrodes count and time the released droplets. A voltage is applied between the electrodes, and a droplet bridging said electrodes allows a current to flow between said electrodes, which current was monitored and processed by an electronic circuit to provide data such as flow rate, total fluid accumulated, etc. While the device described in U.S. Pat. No. 6,640,649 worked well in most applications, there were problems arising from the physical contact of the electrodes with the fluid being metered. The electrodes need calibration, and recalibration at intervals. It was felt that a non-contact system would be preferable, and would operate well using high frequency light pulses, provided adjustment of frequency and light intensity were provided.

It is therefore one of the objects of the present invention to obviate the disadvantages of prior art low-flow meters and to provide a high-frequency optical system which can be adjusted by a technician or by the user.

Yet a further object of the invention is to provide a low-flow meter wherein an automatic system with feedback adjusts frequency and/or strength of the optical system.

It is a further object of the present invention to provide a system that can be relied upon for long term service without needing recalibration.

The present invention achieves the above objectives by providing an optical drop detection system for a low-flow metering device of the type having a drop generator, said system comprising at least one optical transmitter which produces a plurality of light beam pulses of microsecond duration and at millisecond intervals, and at least one optical receiver positioned to register receipt of said light pulses transmitted through the path of drops generated by said drop generator, and to record the number of pulses which hit a given drop and which do not register on said receiver, the frequency and strength of said pulses being calibrated so that a single drop is impinged upon by a plurality of pulses and further comprising automatic feed-back means for adjusting the parameters of interaction between said at least one optical transmitter and said at least one optical receiver to produce and maintain a predetermined minimum and a predetermined maximum number of hits per drop.

In a preferred embodiment of the present invention there is provided an optical drop detection system wherein said optical transmitter produces a plurality of light beam pulses, preferably IR light beam pulses.

In a most preferred embodiment of the present invention there is provided an optical drop detection system wherein said pulses are calibrated so that a single drop is impinged upon by at least 1, or preferably at least 3 pulses.

In further embodiments said pulses are calibrated so that a single drop is impinged upon by up to 20 pulses, preferably by up to 8 pulses.

In a further embodiment, the interval between said pulses is between 0.2 and 50 milliseconds, the most preferred range being between 1 and 10 milliseconds.

In yet a further embodiment, said change in the intensity of the transmitted light beam pulses is effected by use of a variable resistor or amplifier.

In another embodiment said change in the intensity of the transmitted light beam pulses is effected by varying a connection between said at least one optical transmitter and a plurality of amplifiers.

Also another embodiment provides a system wherein the parameters of interaction between said at least one optical transmitter and said at least one optical receiver are varied by changing the frequency of the transmitted light beam pulses.

It will thus be realized that the novel device of the present invention need be calibrated only once, unless of course some change occurs in the fluid being metered. Apart from occasional cleaning, if needed, of the optically active faces, the device is maintenance free.

As will be evident by glancing at FIG. 1, the device can advantageously be used with the drop generator disclosed in U.S. Pat. No. 6,640,649 B1. The electrodes are replaced by a light emitter and a light receiver, which light receiver is attached outside the transparent walls of the housing chamber opposite the emitter, which is also positioned outside the transparent walls of the housing chamber. An electronics control and display housing sends power pulses to the light emitter and meters the corresponding electric output of the receiver. Lack of such output indicates that an interposing droplet of fluid has deflected the light beam from reaching the receiver. As pulse frequency is much faster than droplet generation, the electronics easily distinguishes between a droplet, a gap, and a succeeding droplet. The data generated is electronically converted to flow rate and displayed on a screen. If needed, results can also be printed on paper tape.

In some circumstances there are advantages in using more than one light source and more than one receiver. Such an arrangement is suited to situations where drop generation is fast, and to provide a greater detection range covering more possible angles of falling droplet paths.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Figure 1:
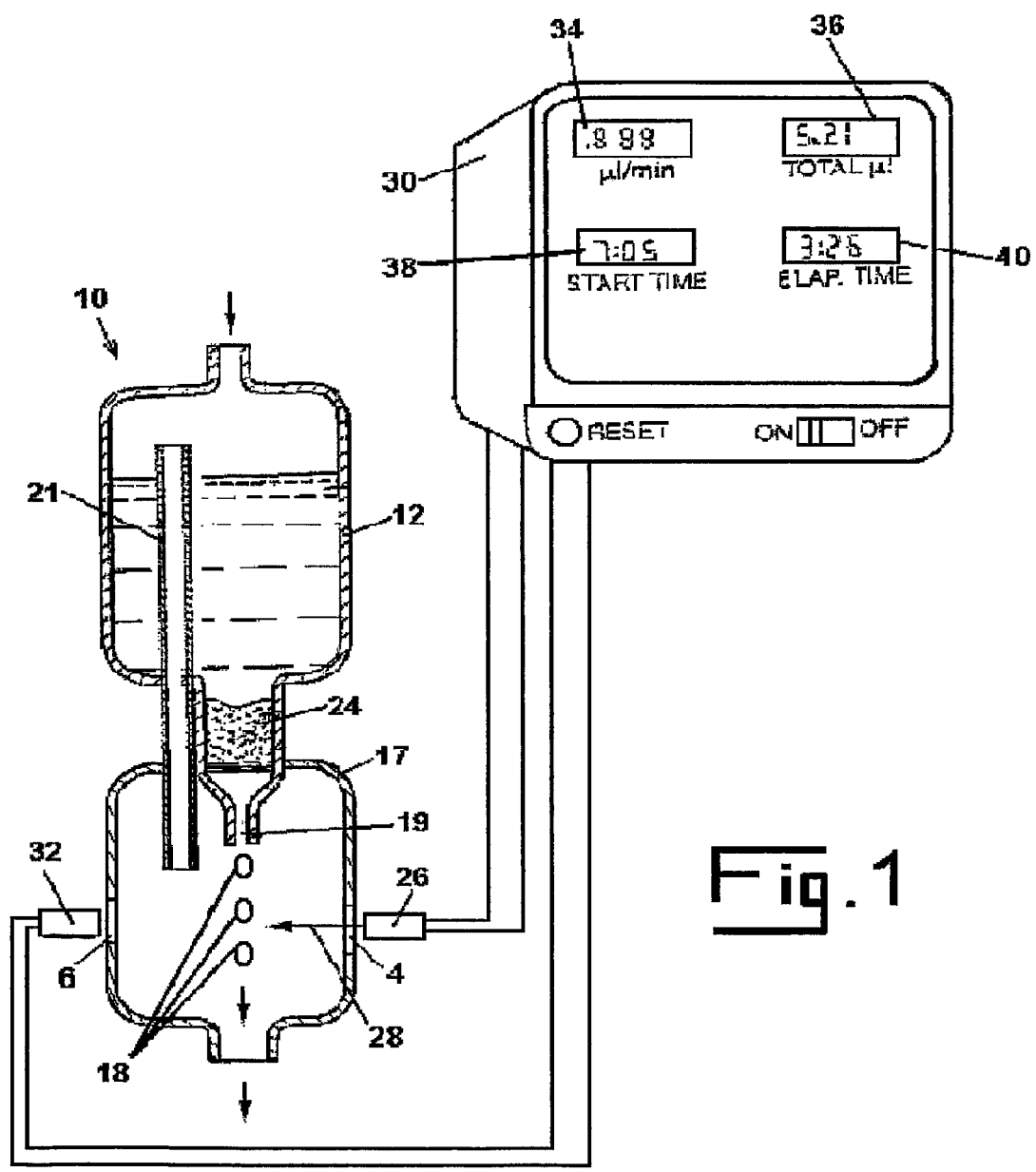
FIG. 1 is a partly sectioned elevational view of a preferred embodiment of the system according to the invention.

There is seen in FIG. 1 an optical drop detection system 10, for a low-flow metering device. The device includes a drop generator. The drop generator seen in the figure has been fully described in U.S. Pat. No. 6,640,649 B1. Although the drop generator is not the central subject of the present invention, components thereof are presented in FIG. 1, for a better understanding of the present invention as it would be applied to such a drop generator, wherein the main components of said drop generator are as follows: first chamber 12 and second chamber 17 having outer transparent walls 4 and 6, droplets 18, orifice 19, overflow and gas pressure equalizer 21, porous substance 24, and electronics 30. The present invention may however be applied to other types of drop generators.

The system shown 10, has an optical transmitter 26, positioned outside of transparent wall 4 of second chamber 17, which produces light beam pulses 28, of microsecond duration and at millisecond intervals. Preferably the light beam pulses 28 are of IR frequency.

An optical receiver 32 is positioned outside of transparent wall 6 of second chamber 17, opposite optical transmitter 26, to register receipt of the light pulses 28, unless it is disturbed by the passage of droplets 18 produced by the drop generator. The electronics 30 record the number of pulses that hit a given drop and due to deflection by a passing drop do not register on the receiver 32.

The frequency and intensity of the light beam pulses 28 are calibrated so that a single drop is impinged upon by a plurality of pulses.

As described hereinbefore, the optical transmitter 26, is pulsed with relatively high power but for extremely short periods of time. The optical receiver 32, sees the generated light beam and registers that it has in fact received said light beam. Thus the optical receiver 32 expects to see the light beam pulse 28 every time a beam is transmitted.

The arrangement is such that when the optical receiver 32 registers receipt of a light pulse 28, it registers a "miss". If however, it does not register receipt of an expected light beam pulse, it registers a "hit".

A falling drop 18, that passes through the beam 28, does not allow every light beam pulse to be registered by the optical receiver 32. However, not every light beam pulse 28, that impinges on a drop, is deflected. There are beams that go through the drop, depending on the angle of impingement and the strength of the light beam pulse. Thus, the light beam pulse can be so strong that it will always be registered and the passage of a drop will not be detected, thus registering a miss, or the light beam pulse can be so weak that more hits are detected then actually occur, due to other circumstances as discussed hereinafter.

Thus, the arrangement is such that if the light beam pulse 28, hits a drop 18 at a certain critical angle, then it is deflected and the beam will not be detected by the optical receiver 32, which is registered as a "hit". If the light beam pulse impinges on the drop at angles other than the predetermined critical angle, then the light beam will pass through the drop, will be received by the optical receiver 32, and registered as a "miss" rather than a "hit".

As will be realized, each drop 18 that falls, cuts the light pulse beam 28 in different ways depending on the strength of the pulse beam, the frequency of the pulses, etc.

According to the present invention, there is selected an arbitrary representative number of drops, from between e.g. 3-30 for calibrating a predetermined minimum and maximum number of hits for the particular system.

Thus for example, a first drop may be impinged upon by a plurality of pulses 28, resulting in the optical receiver 32 recording 5 hits, while the next drop 18 is also impinged upon by a plurality of pulses 28, but because of the timing of the passage of the drop relative to the timing of the pulses, the optical receiver 32 only records 3 hits. The following drop could result in the recording of, e.g., 4 hits. Once a maximum and minimum number of hits are recorded over a chosen sample of drops, then the system can be calibrated and set for a number for minimum hits and a number of maximum hits, which is normal for the system.

Depending on the frequency of the pulse beams and the speed of the drop, it is possible to have, e.g., up to 8 potential pulse beams that can impinge on and detect a single drop.

With such a calibration, if the optical receiver 32, records 8 hits for each drop, then every drop was impinged upon 8 times in a manner that resulted in the interruption of the light beam pulse.

If more than 8 hits were recorded per drop on such a precalibrated system, then, it is known that there is something wrong which needs to be corrected, and such potential faults include:

a) the existence of dirt on walls 4 or 6 of chamber 17,
b) the existence of a droplet on one of the walls 4 or 6 of chamber 17 within the path of light pulse 28,
c) the formation of mist on one or both of the walls 4 or 6 of chamber 17; or
d) the light beam was too weak.

Alternatively, if the minimum number of hits for a drop is not recorded and registered by optical receiver 32, it means that at least one drop was "missed", which could indicate that the strength of the light beam pulse 28 is excessive which would also require recalibration according to the present invention.

As will be discussed with reference to FIG. 2, the present invention provides a feedback loop whereby the strength of the light beam pulses may be adjusted according to actual registration of receipt of the minimum and/or maximum hits. Thus a weak beam is detected by the recording of a higher number of maximum hits than that precalibrated for the system, and a strong beam is detected by a lower number of minimum hits than that precalibrated for the system, as described hereinbefore.

More specifically, as will now be understood, when the light beam is stronger, then more light will pass through the drop, and the number of recorded hits is reduced. If however, the light beam is weaker, then the drop or the chamber walls will allow less light to pass through, and the number of recorded hits will increase.

Thus, once a system has been calibrated as to its normal average minimum and maximum number of hits per drop, then, if over time, the system is registering a lower amount of hits than the normal average minimum, then the power of the system can be reduced to increase the number of hits being registered, while if over time the system is registering a higher amount of hits than the normal average maximum, the power of the system is increased in order to decrease the number of hits, as discussed with regard to FIGS. 2-5 hereinafter.

Figure 2:
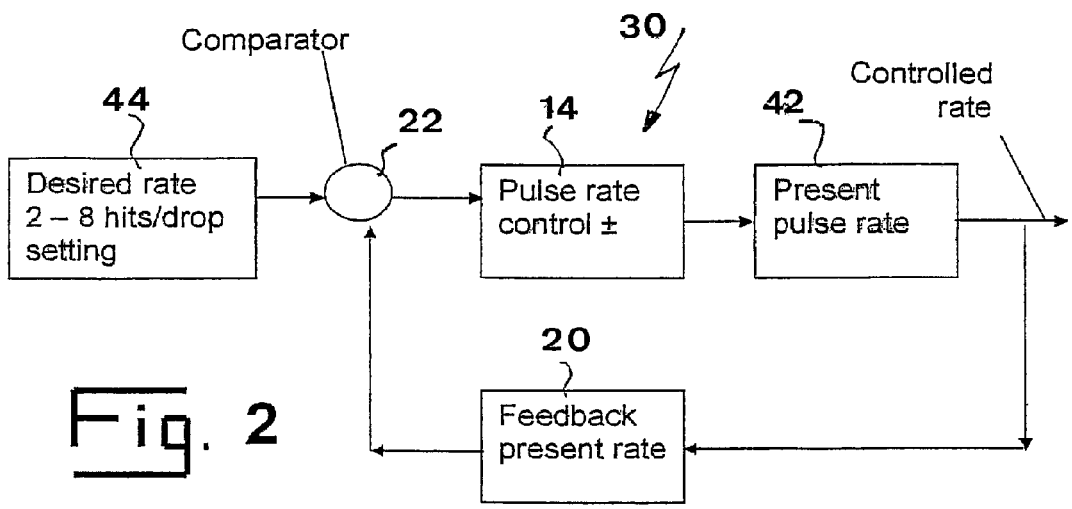
FIG. 2 is a block diagram relating to feedback control of the same embodiment as seen in FIG. 1.

As seen in FIG. 2, the system electronics 30 provides for automatic feed-back means for adjusting the parameters of interaction, such as the present pulse rate 42 and the desired pulse rate 44 of the optical transmitter 26.

The optical receiver 32 seen in FIG. 1 is to produce and maintain a predetermined minimum and a predetermined maximum number of hits per drop.

A feedback line informs the comparator 22 of the present rate and the comparator 22 then signals the pulse rate control 14 to reduce the difference between the new and desired value.

A pulse beam rate control 14 increases/decreases the pulse rate and intensity strength to conform to a desired number of hits per droplet.

The display screen shows the calculated flow rate 34, total accumulated flow 36, starting time 38, elapsed time 40, and other data as needed.

With regard to the rest of the figures, similar reference numerals have been used to identify similar parts.

Figure 3:
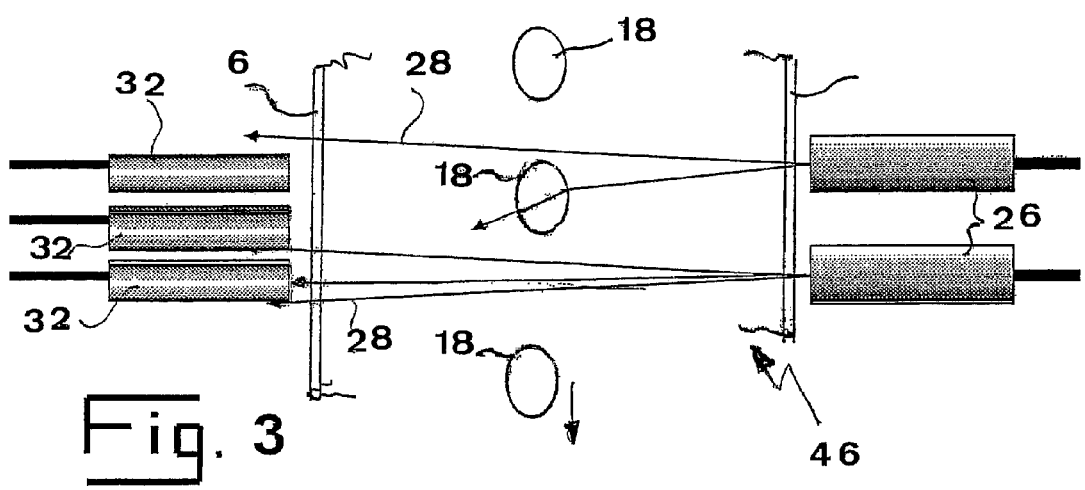
FIG. 3 is a diagrammatic view of an embodiment using several transmitters and receivers.

FIG. 3 represents an optical drop detection system 46 wherein two optical transmitters 26 produce a plurality of IR light beam pulses 28, which are received by three closely-spaced optical receivers 32. Droplets 18 fall between the transmitters 26 and the receivers 32 and deflect the light beam pulses 28, the results being processed electronically to calculate the flow rate 34 seen in FIG. 1.

Figure 4:
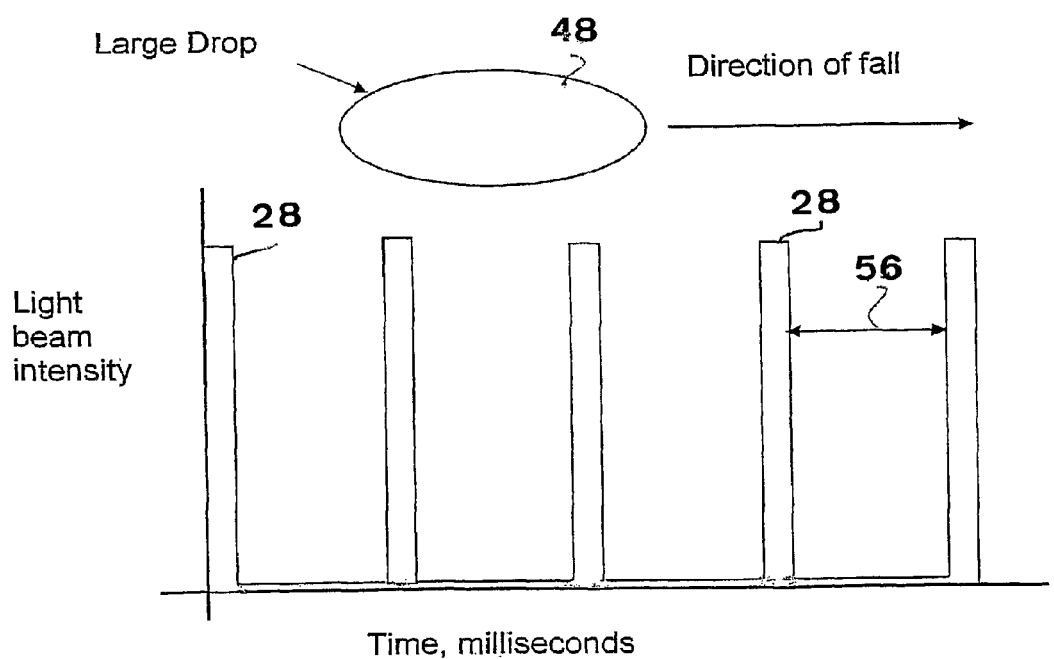
FIG. 4 is a graphical representation of a drop and a pulsed light beam and a large drop.

Turning now to FIG. 4 there is seen a graphical representation of a drop detection system wherein the light beam pulses 28 are calibrated so that a single drop 48 is impinged upon by at least 2 pulses and preferably by at least 3 pulses and at most by 8 pulses. The hits are dependent on the strength of the light pulses 28 passing through or being stopped by the drops 48.

A dark interval 56 between pulses is between 0.2 and 50 milliseconds, and preferably the interval between the pulses is between 1 and 10 milliseconds.

Figure 5:
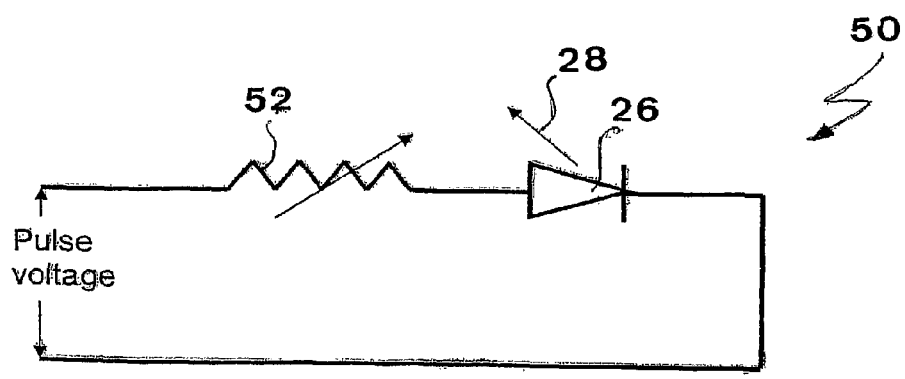
FIGS. 5, 6 and 7 are circuit diagrams showing different methods of modulating the light beam pulses.

Referring now to FIG. 5 there is seen a circuit of a further optical drop detection system 50 wherein the parameters of interaction between the optical transmitter 26 and the optical receiver 32, seen in FIG. 1, are varied by changing the intensity of the transmitted light beam pulses 28. In the present embodiment the change in the intensity of the transmitted light beam pulses 28 is effected by a variable resistor 52 or amplifier (not shown).

Figure 6:
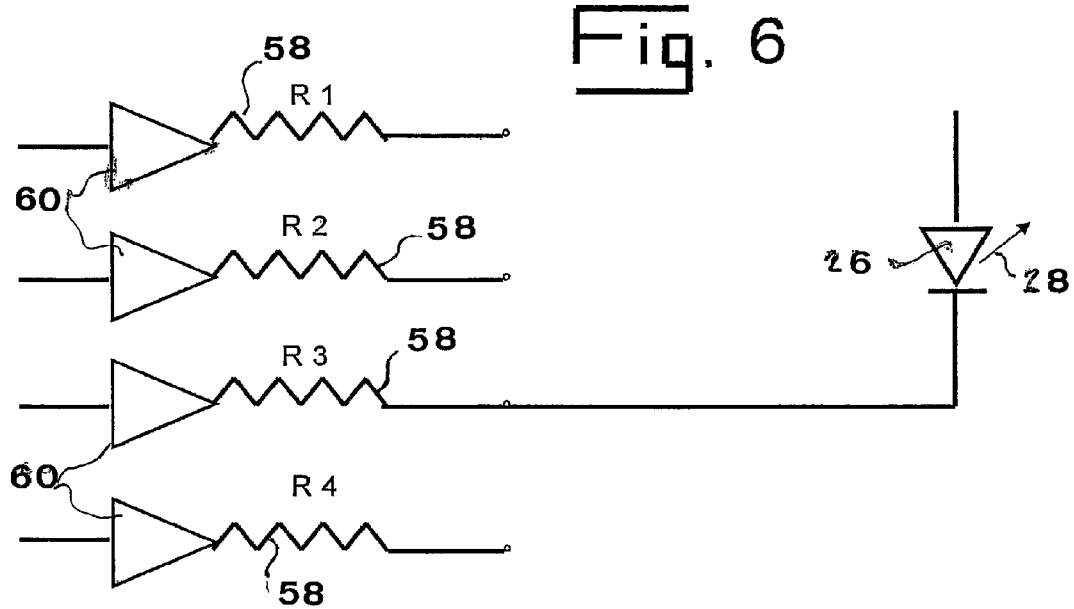

FIG. 6 is a circuit diagram referring to an embodiment wherein the change in the intensity of the transmitted light beam pulses 28 is effected by varying a connection between the optical transmitter 26 and a plurality of resistors 58 (R1, R2, R3, R4) of different values and amplifiers 60.

Figure 7:
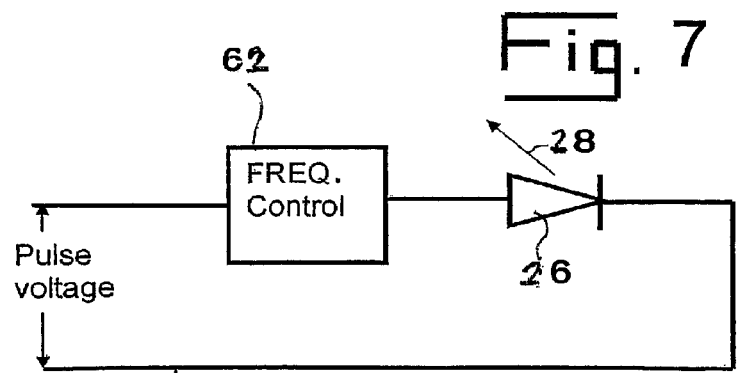

FIG. 7 illustrates a detail of an optical drop detection system wherein the parameters of interaction between the optical transmitter 26 and the optical receiver 32 (seen in FIG. 1) are varied by changing the frequency of the transmitted light beam pulses 28 by means of a frequency controller 62

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An optical drop detection system for a low-flow metering device of the type having a drop generator, said system comprising at least one optical transmitter which produces a light beam, and at least one optical receiver positioned to register receipt of said light beam transmitted through the path of drops generated by said drop generator, and further comprising an automatic feed-back system for adjusting the parameters of interaction between said at least one optical transmitter and said at least one optical receiver to produce and maintain a predetermined amount of light being registered by said at least one optical receiver per drop, wherein said light beam comprises plurality of light beam pulses, wherein said at least one optical transmitter produces said plurality of light beam pulses and said at least one optical receiver records the number of pulses which hit a given drop and which do not register on said receiver.

2. The system of claim 1, wherein said optical transmitter is located opposite to said optical receiver.

3. The system of claim 1, wherein said feedback provided by said automatic feedback system further comprises signalling to adjust the intensity of said light beam as one of the parameters of interaction.

4. The system of claim 3, wherein said automatic feedback system further comprises a comparison system.

5. The system of claim 4, further comprising a variable resistor or amplifier for adjusting the intensity of said light beam, wherein said comparison system signals said variable resistor or amplifier.

6. The system of claim 4, further comprising a plurality of amplifiers, wherein said comparison system signals to vary a connection between said at least one optical transmitter and a plurality of amplifiers.

7. The system of claim 1, wherein said automatic feedback system adjusts the parameters of interaction to maintain a predetermined minimum or a predetermined maximum number of hits per drop, or a combination thereof.

8. The system of claim 7, further comprising a pulse beam rate control to adjust one or more of intensity of light or pulse rate of light according to a signal from said automatic feedback system.

9. The system of claim 1, wherein said light beam comprises IR (infra-red) light.

10. The system of claim 1, further comprising a display to show one or more of a calculated flow rate or a total accumulated flow.

11. The system of claim 1, wherein said optical transmitter is a single optical transmitter and said optical receiver is a single optical receiver.

12. The system of claim 1, wherein said optical transmitter is a plurality of optical transmitters and said optical receiver is a plurality of optical receivers, if drop generation is fast, or to provide a greater detection range covering more possible angles of falling droplet paths, or a combination thereof.

13. An optical drop detection system for a low-flow metering device of the type having a drop generator, said system comprising at least one optical transmitter which produces a light beam, at least one optical receiver positioned to register receipt of said light beam transmitted through the path of drops generated by said drop generator, an automatic feed-back system for adjusting the parameters of interaction between said at least one optical transmitter and said at least one optical receiver to produce and maintain a predetermined amount of light being registered by said at least one optical receiver per drop, wherein said automatic feedback system further comprises a comparison system, and a plurality of amplifiers for adjusting the intensity of said light beam, wherein said comparison system signals to said plurality of amplifiers to vary a connection between said at least one optical transmitter and said plurality of amplifiers.

* * * * *